(12) United States Patent
Dupps, Jr. et al.

(10) Patent No.: US 8,812,280 B2
(45) Date of Patent: *Aug. 19, 2014

(54) METHOD FOR MODELING BIOMECHANICAL PROPERTIES OF AN EYE

(71) Applicant: The Cleveland Clinic Foundation, Cleveland, OH (US)

(72) Inventors: William J. Dupps, Jr., Bay Village, OH (US); Abhijit Sinha Roy, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/731,255

(22) Filed: Dec. 31, 2012

(65) Prior Publication Data
US 2013/0138400 A1 May 30, 2013

Related U.S. Application Data

(63) Continuation of application No. 12/429,149, filed on Apr. 23, 2009, now Pat. No. 8,346,518.

(60) Provisional application No. 61/047,179, filed on Apr. 23, 2008.

(51) Int. Cl.
*G06G 7/48* (2006.01)

(52) U.S. Cl.
USPC .................. 703/6; 351/237; 351/200

(58) Field of Classification Search
USPC ........................ 703/6; 351/237, 200
See application file for complete search history.

(56) References Cited

U.S. PATENT DOCUMENTS

| 6,302,540 B1* | 10/2001 | Katzman et al. ......... 351/159.74 |
| 2003/0107706 A1* | 6/2003 | Rubinstein et al. ........... 351/177 |
| 2007/0162265 A1* | 7/2007 | Hall ................................. 703/3 |
| 2008/0086048 A1* | 4/2008 | Dupps et al. ................... 600/405 |

* cited by examiner

*Primary Examiner* — Dwin M Craig
(74) *Attorney, Agent, or Firm* — Tarolli, Sundheim, Covell & Tummino LLP (57) ABSTRACT

Systems and methods are provided for predicting the results of a therapeutic intervention to an eye. An imaging system is configured to provide image data representing at least a portion of the eye of the patient. An input device is configured to permit a user to design a proposed therapeutic intervention for the eye of the patient. A finite element modeling component is configured to generate a finite element model representing the condition of the eye of the patient after the proposed therapeutic intervention according to the image data, the proposed therapeutic intervention, and at least one biomechanical property of tissue comprising the eye. The generated model is constructed as to have no a priori restraints on the motion of the corneal limbus. A display is configured to display the generated model to the user.

15 Claims, 6 Drawing Sheets

METHOD FOR MODELING BIOMECHANICAL PROPERTIES OF AN EYE

RELATED APPLICATIONS

This application is a Continuation of and claims priority to U.S. patent application Ser. No. 12/429,149 filed Apr. 23, 2009, now U.S. Pat. No. 8,346,518, which in turn claims priority from U.S. Provisional Application No. 61/047,179, filed Apr. 23, 2008. The entirety of the subject matter of these applications is incorporated herein by reference.

FIELD OF THE INVENTION

The present invention relates to systems and methods for evaluating the condition and properties of a mammalian eye, and, in particular, is directed to systems and methods for in vivo modeling of biomechanical properties of the eye.

BACKGROUND OF THE INVENTION

The cornea relies greatly upon its material properties in its roles as a mechanical barrier to injury and as a scaffold for the eye's primary refracting surface. These biomechanical properties influence the safety and optical predictability of surgery and play an important role in the pathogenesis and of diseases such as keratoconus and post-refractive surgery ectasia. Consequently, alteration of these properties by disease or surgery can have profound visual implications. Ectatic diseases such as keratoconus, pellucid marginal degeneration and keratoglobus are characterized by progressive thinning and distortion of the cornea, and as a class represent a leading indication for corneal transplantation. Identification of early ectasia is a major emphasis of preoperative refractive surgery evaluations, where it is imperative to avoid the potential destabilizing effects of laser vision correction in corneas that are predisposed to biomechanical instability or failure.

SUMMARY OF THE INVENTION

In accordance with an aspect of the present invention, a system is provided for predicting the results of a therapeutic intervention for an eye of a patient. An imaging system is configured to provide image data representing at least a portion of the eye of the patient. An input device is configured to permit a user to design a proposed therapeutic intervention for the eye of the patient. A finite element modeling component is configured to generate a finite element model representing the condition of the eye of the patient after the proposed therapeutic intervention according to the image data, the proposed therapeutic intervention, and at least one biomechanical property of tissue comprising the eye. The generated model is constructed as to have no a priori restraints on the motion of the corneal limbus. A display is configured to display the generated model to the user.

In accordance with another aspect of the present invention, a computer readable medium, storing executable instructions for facilitating the design of a therapeutic intervention for an eye of a patient, is provided. The executable instructions include a geometry generation element that is configured to forms a three-dimensional representation of the eye of the patient from received image data. A user interface is configured to receive a plurality of therapeutic parameters defining a proposed therapeutic intervention for the eye of the patient from an associated input device. A reconciliation engine is configured to establish a finite element model of the eye of the patient according to the determined geometry of the eye and at least one biomechanical parameter of the model for each of the cornea, the sclera, the corneal limbus, and the at least one other structure, alter at least one of a biomechanical parameter and the determined geometry of the eye according to the therapeutic parameters, and solve the established model to determine a predicted geometry of the eye after the therapeutic intervention. An optical characterization component is configured to calculate at least one optical parameter from the predicted geometry.

In accordance with yet another aspect of the present invention, a method is provided for predicting the results of one of a therapeutic intervention for an eye of a patient. At least a portion of the eye of the patient is scanned by an imaging system to provide image data representing the eye. A three-dimensional representation of the eye of the patient is generated from the image data. A finite element model of the eye of the patient is established according to the determined geometry of the eye and at least one biomechanical parameter of the model for each of the cornea, the sclera, the corneal limbus, and the at least one other structure. The established model has no a priori restraints on the motion of the corneal limbus. At least one of a biomechanical parameter and the determined geometry of the eye is altered according to input from a user. A predicted geometry of the eye after the therapeutic intervention is determined according to the altered model. The predicted geometry is displayed to the user.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION OF THE INVENTION

Figure 1:
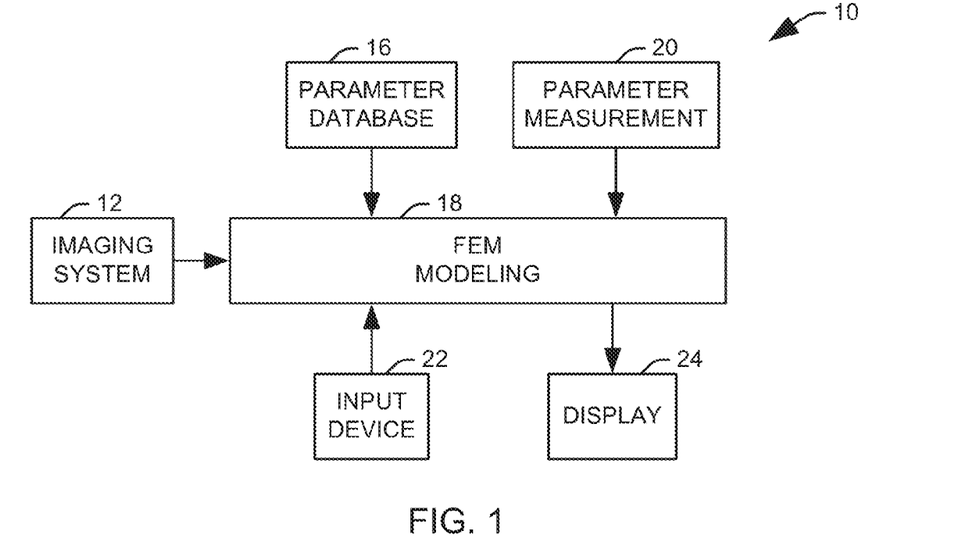
FIG. 1 illustrates a system for generating a predicted condition of a patient's eye in view of a proposed therapeutic procedure based on a biomechanical model of the eye.

FIG. 1 illustrates a system 10 for generating a predicted condition of a patient's eye in view of a proposed therapeutic procedure based on a biomechanical model of the eye. In accordance with an aspect of the present invention, the system 10 utilizes a whole eye representation of the eye to determine the forces and stresses applied to the corneal tissue. Accordingly, predicted shape, specifically the corneal shape, is influenced by properties of portions of the eye other than the cornea, sclera, and the cornea-sclera boundary (i.e., the corneal limbus). The system 10 comprises an imaging component 12 that is configured to provide a representation of a patient's eye. The imaging component 12 can utilize magnetic resonance imaging (MRI), optical coherence tomography (OCT), Scheinpflug imaging, or any other appropriate imaging modality. The determined images can be supplemented by additional values, such as a measured corneal topography and a determined axial length of the eye. To this end, the elastography imaging device 32 can include, for example, an ultrasound imaging device or a partial coherence interferometer arrangement, for determining the axial length, as well as an appropriate imager for determining the corneal topography. It will be appreciated that, while the system 10, focuses on the effects of surgical and therapeutic intervention on the corneal and the resulting visual effects, the representation of the patient's eye can further include each of the sclera, the lens, the zonules, the choroid, the retina, the iris and, the ciliary body of the eye.

The images provided by the imaging component 12 can be digitized and processed as to obtain an overall geometry of the eye. For example, the images can be filtered and one or more edge detection algorithms can be utilized to determine the boundaries of the various tissue layers. Once the boundaries of the various tissue components is established, the processed image data can be provided to a finite element modeling (FEM) component 18 that establishes a finite element model of the ocular tissue according to the determined geometry of the eye and one or more biomechanical parameters, which can include parameters such as Poisson's ratio and Young's modulus, as well as non-linear measures of elasticity, such as hysteresis, creep, stress relaxation, and a strain dependent function for Young's modulus, for each of the tissue types. In accordance with an aspect of the present invention, the calculated FEM modeling of the eye tissue does not include a priori restraints on the corneal limbus, such that the boundary between the cornea and sclera is free to move in response to stresses from other locations within the whole eye model. By modeling the limbus as a flexible reinforcing structure that maintains corneal curvature in response to intraocular pressure changes under physiological conditions, the effects of extracorneal structures on the corneal shape can be incorporated into the model.

In the illustrated implementation, one or more biomechanical parameters specific to the patient can be determined at a parameter measurement system 20. For example, the parameter measurement system 20 can include an imaging system that detects a deflection of one or more regions of tissue under an applied stress. Alternatively, a more precise measurement for the biomechanical parameters, including spatial variance in the parameters across the tissue types, can be determined using a device, such as that described in U.S. Published Patent Application No. 2008/0086048, that can be utilized to determine biomechanical properties of the cornea, including non-linear measures of elasticity, at each of a plurality of locations. In this implementation, the data from the imaging system 12 and the elastography data can be used at the FEM component 18 to generate the finite element model of the cornea, including displacements and strains on the corneal tissue from other portions. Alternatively, the parameter measurement system 20 can provide the biomechanical parameters as spatially varying functions of one or more parameters across a portion of the eye (e.g., the cornea and sclera), with the finite element modeling component 18 utilizing the functions to model the biomechanical properties of the tissue. For example, the gradient of a non-linear measures of viscoelasticity, such as hysteresis, stress relaxation, or creep can be determined in one or more directions, and a function describing the change in the nonlinear viscoelasticity can be derived (e.g., via a regression analysis) from the collected data.

Figure 2:
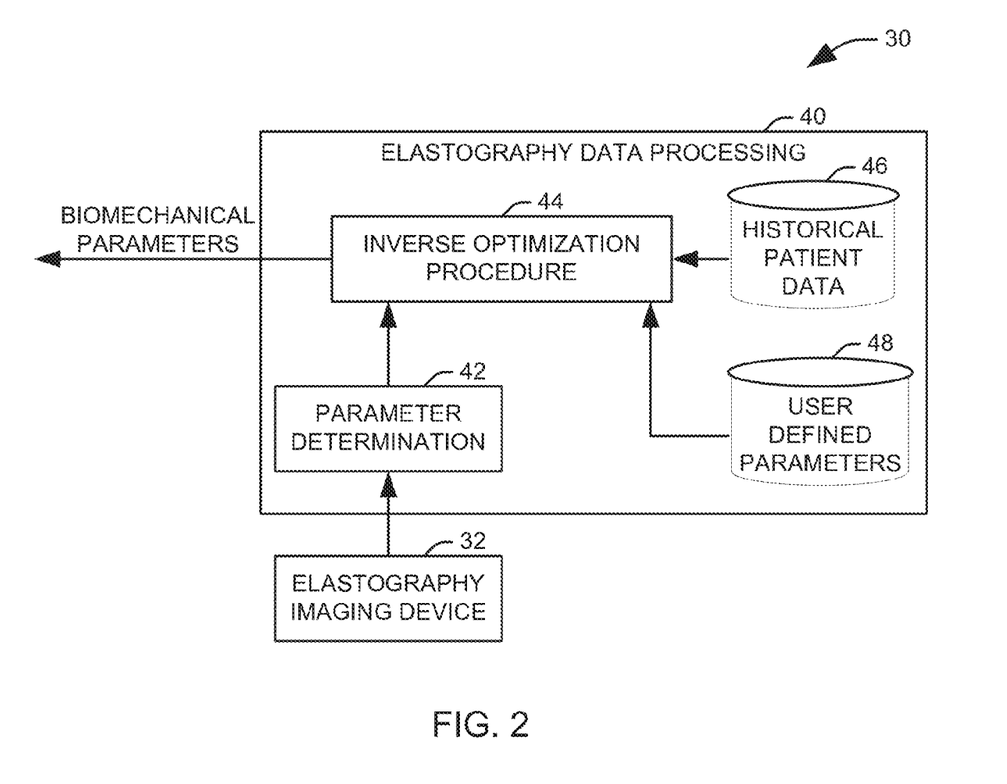
FIG. 2 illustrates one example of a system configured to provide patient specific biomechanical parameters for the eye of a patient in accordance with an aspect of the present invention.

FIG. 2 illustrates one example of a system 30 configured to provide patient specific biomechanical parameters for the eye of a patient in accordance with an aspect of the present invention. An elastography imaging device 32 is configured to apply a perturbation to at least a portion of the eye tissue and measure a displacement of the eye tissue in response to the perturbation at each of a plurality of locations. A "perturbation" can include any of a known force, pressure, energy, or displacement applied to the eye tissue as to cause a displacement of the eye tissue. The elastography imaging device 32 can comprise an apparatus for applying the perturbation to the eye tissue, for example, pneumatically, acoustically, or via a mechanical force (e.g., applanation). The eye tissue can be imaged before and after the force is applied, or at a plurality of different forces, to provide a plurality of images of the eye. The imaging device can utilize magnetic resonance imaging (MRI), optical coherence tomography (OCT), Scheinpflug imaging, or any other appropriate imaging modality. The determined images can be supplemented by additional values, such as a measured corneal topography and a determined axial length of the eye. To this end, the elastography imaging device 32 can include, for example, an ultrasound imaging device or a partial coherence interferometer arrangement, for determining the axial length, as well as an appropriate imager for determining the corneal topography.

The data from the elastography imaging device 32 can be provided to a data processor 40. The data processor 40 is configured to determine the at least one biomechanical property of the eye that is specific to the patient according to the measured displacement and the measured force. The data processor 40 includes a parameter determination component 42 that determines biomechanical parameters for the eye tissue according to the provided image data. In one implementation, a known displacement can be applied to the cornea in a first direction, and the displacement of the cornea in second and third directions, each perpendicular to the first direction and to one another, can be measured at a plurality of locations. For each location, a ratio of the measured displacement along the second direction to the known displacement along the first direction and a ratio of the measured displacement along the third direction to the known displacement along the first direction can be determined and provided as biomechanical parameters for the location.

In another implementation, the displacement of the cornea in response to a known force can be utilized to measure stress and strain parameters of the cornea. For a given measured displacement, d, of the cornea, a force, F, can be determined such that F is a function of d. A parameter, g, represents the difference between the known force, F, and an expected force from the displacement, f(d), such that $g = F - f(d)$.

The cornea is modeled as an anisotropic, non-linear, viscoelastic and hyperelastic material with layers of collagen fibrils oriented orthogonally in the center and circumferentially near the limbus. While the cornea has several layers of tissue, the stroma is the thickest and the primary load bearing component of the cornea. Thus, the cornea can be reduced in the finite element model to a continuum tissue using a general equation of the form: $\sigma = E\epsilon + \eta\dot{\epsilon}$, where $\sigma$, $\epsilon$, and $\eta$ are the stress tensor, strain tensor, and time derivative of strain tensor, respectively E and $\eta$ are the elastic and viscous components of the viscoelastic properties of the tissue. E can be constructed as a non-linear function of $\epsilon$ computed along the direction of fibers, [A1, A2], in the plane of deformed cornea. Here A1 and A2 are the direction cosines of the two predominant families of collagen fibers in the cornea such that A1·A2=0 (representing orthogonality). Further, the cornea is modeled as a hydrated tissue and has negative fluid pressure acting on the collagen fibrils. This negative fluid pressure can be included in the stress tensor by the following equation: $\sigma = \sigma - pI$, where p is the fluid pressure and I is the identity matrix. In general, p is of the order of 50-60 mmHg in the cornea.

The sets of equations g and $\sigma$ will be solved in an inverse optimization procedure 44 in which, for the measured forces and strain in the elastography tool, the stresses will be computed. It will be appreciated that the inverse optimization procedure 44 can be trained on a database 46 of historical patient data and utilize a database 48 of stored parameters defined by a user. The inverse optimization procedure then determines the non-linear elastic and viscous properties, [E, $\eta$] of the tissue iteratively until both g and $\sigma$ are constrained to the desired user defined tolerance. Once [E, $\eta$] are obtained for the pre-operative cornea, these biomechanical parameters can be provided to a finite element modeling component in accordance with an aspect of the present invention to generate a post-operative scenario of the cornea. The post-operative viscoelastic properties can be determined by perturbing the elastic and viscous properties as to simulate a therapeutic procedure. The perturbed values of [E, $\eta$] can then be provided to the FEM model to simulate post-surgery shape and optical parameters (power, Zernike wavefronts).

Returning to FIG. 1, once a geometry for the eye and biomechanical parameters for the tissue have been established, individual parameters for the finite elements comprising the model can be altered by a user at an input device 22, such as to simulate a therapeutic intervention. For example, a user can alter one or both of the thickness or biomechanical properties of the model for a given region of tissue as to simulate a therapeutic procedure, such as refractive surgery or collagen stiffing of the corneal tissue. The altered model can then be reconciled to calculate an overall shape of the eye, with an emphasis on the cornea and sclera. From the determined shape, one or more optical parameters, such as optical power values and Zernike polynomials characterizing the shape of the cornea, can be determined and provided to the user, along with the calculated shape of the eye at a display 24.

In one implementation, the FEA model can be reduced to a model of the cornea and sclera, with the forces exerted by the other tissue layers represented as an external force on the cornea tissue. Accordingly, while this reduced model does not directly incorporate extracorneal tissue into the model, known effects that have been characterized from the whole eye model can be incorporated into the model to maintain the influence of structures other than the cornea and sclera on the corneal shape. It will be appreciated that the force representing the effects of the extracorneal structures can be determined according to specific characteristics of a patient's eye, including known geometric properties derived from the image data as well as any biomechanical properties of the extracorneal tissue determined at the parameter measurement system 20.

Further, in accordance with an aspect of the present invention, the determined model can be corrected for intraocular pressure (TOP) such that the changes applied to simulate a therapeutic procedure are applied to an "inverse model" that is adjusted to reflect the condition of the patient's eye absent intraocular pressure. Once the changes have been applied, the reconciled model can be adjusted to include an appropriate value for the patient for intraocular pressure. It will be appreciated that the influence of intraocular pressure on the corneal shape can be significant, and has been determined, through use of a whole eye model in accordance with an aspect of the present invention, to depend greatly on the material properties of the cornea. Accordingly, the results of a therapeutic intervention, particularly refractive surgery, can vary significantly according to the stiffness of the corneal tissue and the intraocular pressure of the eye.

Figure 3:
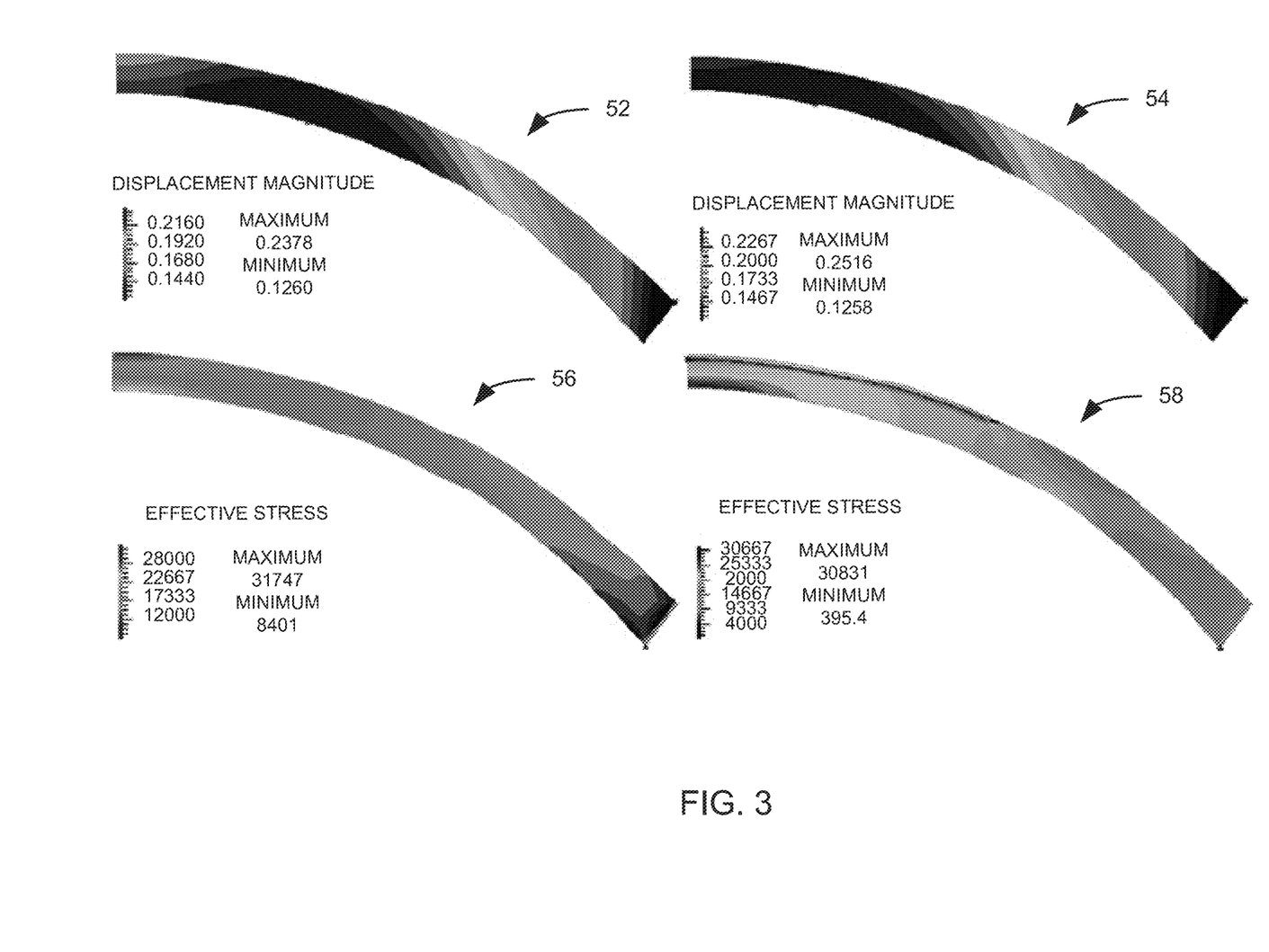
FIGS. 3 and 4 comprise a series of charts illustrating the impact of corneal material properties on the post surgical deflection of the cornea in a whole eye model in accordance with an aspect of the present invention.
Figure 4:
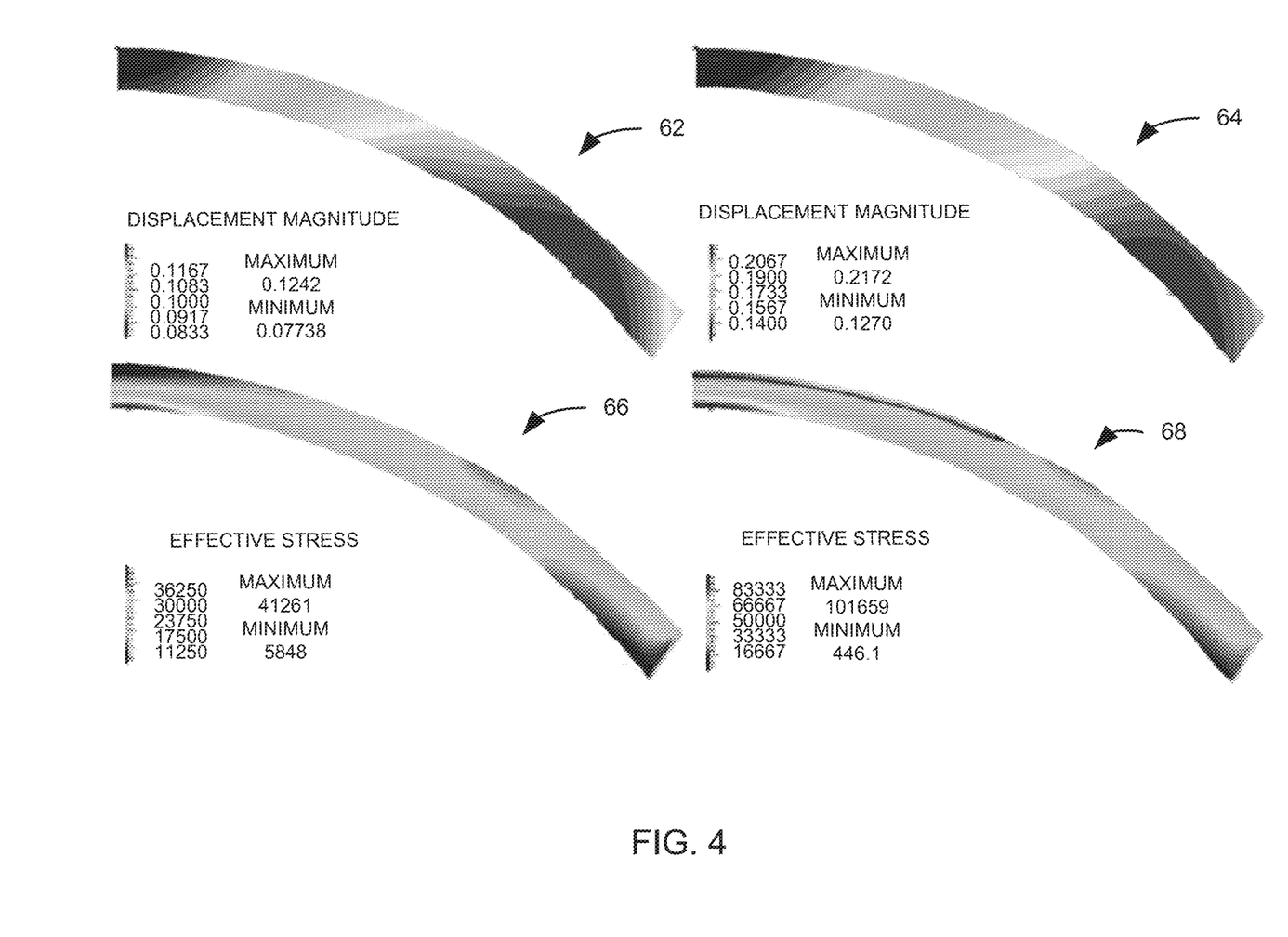

FIGS. 3 and 4 illustrate the impact of corneal material properties on the post surgical deflection of the cornea in a whole eye model in accordance with an aspect of the present invention. FIG. 3 illustrates the modeled change in strain and displacement caused by intraocular pressure in a first cornea, having a low stiffness value, before and after a 6 Diopter LASIK procedure. In the illustrated charts 52, 54, 56, and 58, the intraocular pressure utilized in the model is equal to 15 mmHg. A first chart 52 illustrates the displacement of the cornea before the procedure, and a second chart 54 illustrates the postsurgical displacement. As will be appreciated from the charts 52 and 54, displacements are greatest in the paracentral cornea. Owing to differential central ablation, the LASIK procedure results in a central shift in the location of peak displacement towards the axis. A third chart 56 displays the distribution of stress across the presurgical cornea, and a fourth chart 58 displays the distribution of stress on the cornea after the surgery. Of specific interest is the effective stress distribution (von•Misses stress) in the two models near the anterior surface. A distinct stress discontinuity can be seen in the fourth chart 58, representing the postsurgical cornea, due to the presence of the interface.

FIG. 4 illustrates the modeled change in strain and displacement caused by intraocular pressure in a second cornea, having a high stiffness value, before and after the 6 Diopter LASIK procedure. As in the previous models, the intraocular pressure used in the model for each chart 62, 64, 66, and 68 is equal to 15 mmHg. A first chart 62 illustrates the displacement of the high stiffness cornea before the procedure, and a second chart 64 illustrates the postsurgical displacement. In these charts 62 and 64, it can be seen that peak displacement occurs near the limbus both before and after surgery, as the cornea is stiffer than the posterior segment of the globe in these models. A third chart 66 displays the distribution of stress across the presurgical cornea, and a fourth chart 68 displays the distribution of stress on the cornea after the surgery. As can be seen in both FIGS. 3 and 4, concentrated stresses develop in all models in the central cornea after 6-D LASIK. The stress distributions 66 and 68 in the stiffer cornea 252 are similar to those in FIG. 3, although the magnitudes are higher.

Figure 5:
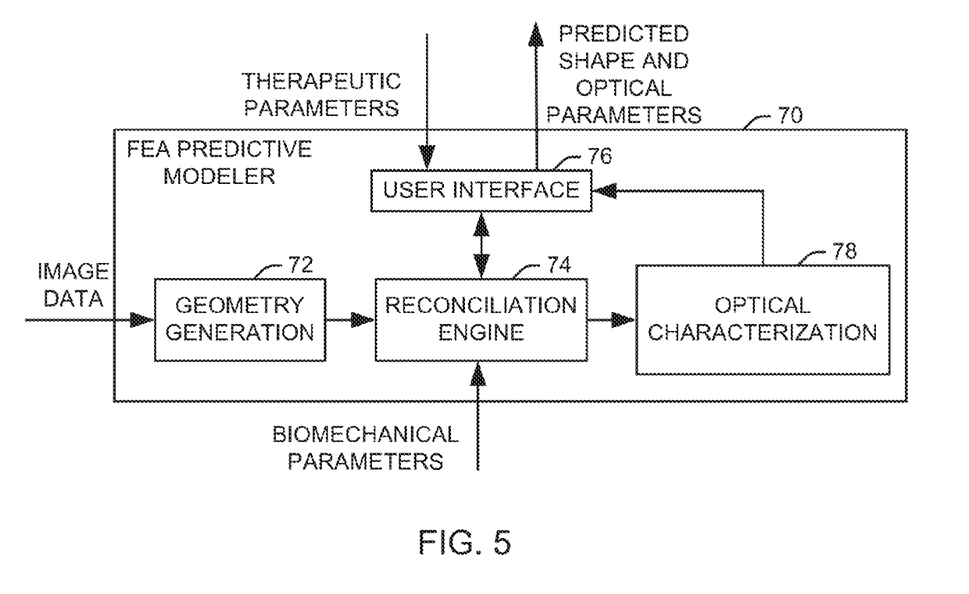
FIG. 5 illustrates a functional block diagram of a finite element analysis predictive modeler that predicts the results of a therapeutic intervention on a patient's eye according to a finite element analysis of the eye.

FIG. 5 illustrates a functional block diagram of a finite element analysis (FEA) predictive modeler 50, stored on as computer executable instructions on computer readable medium, that is executable to predict the results of a therapeutic intervention on a patient's eye according to a finite element analysis (FEA) of the eye. Each functional block illustrated in the diagram represents a series of executable instructions stored in the computer readable medium configured to perform the described function. It will be appreciated, however, that the various functional blocks can be configured to utilize functional instructions from an associated operating system or other common library sources in executing their associated functions. The illustrated FEA predictive modeler 50 receives data representing the eye of a given patient and constructs a model based on this data. A user can select a customized therapeutic intervention for the eye, represented as a series of therapeutic parameters. From the constructed model and the therapeutic parameters, a predicted shape of the eye, given the therapeutic intervention, can be determined. The predicted shape and at least one optical parameter calculated from the shape can be provided to the user at an associated display to illustrate the predicted surgical outcome to the user.

The FEA predictive modeler 70 receives image data representing the patient's eye at a geometry generation element 72. It will be appreciated that the image data can be provided directly from an imaging system, such a computer tomography (CT) system or a magnetic resonance imaging (MRI), or provided to the predictive modeler 70 as data stored on a computer readable medium. The geometry generation element 72 forms a three-dimensional representation of the patient's eye from the image data. For example, a two-dimensional image can be rotated to form a three-dimensional representation of the eye. The thicknesses of the various tissue layers can be provided as parameters from an associated database (not shown). Where the imaging modality allows for a three-dimensional image of the eye, the geometry can be determined directly from the image.

Once the boundaries of the various tissue components is established, the processed image data can be provided to a reconciliation engine 74 that establishes a finite element model of the ocular tissue according to the determined geometry of the eye and one or more biomechanical parameters for each of the tissue types. For example, the biomechanical parameters for the cornea can include parameters such as Poisson's ratio and Young's modulus, as well as non-linear measures of elasticity, such as hysteresis, creep, stress relaxation, and a strain dependent function for Young's modulus, for each of the corneal tissue generally and for flap wounds in the cornea. These values can be taken from known average values for the appropriate tissue types or determined directly from the patient for one or more tissue types via measurement of the tissue properties under stress. It will be appreciated, however, in accordance with an aspect of the present invention, that where spatial variance of the biomechanical properties of the tissue from the average can be ascertained, individualized values can be used for the various finite element values within a given tissue type.

Once the geometry and biomechanical properties for the various finite elements comprising the model have been established, selected elements can be altered by a user at a user interface 76 to represent a therapeutic intervention. For example, a user can alter one or both of the thickness or biomechanical properties of the model for a given region of tissue as to simulate a therapeutic procedure, such as LASIK flaps or regions of cornea exposed to a collagen cross-linking agent. In accordance with an aspect of the present invention, a set of standard therapeutic patterns can be provided as part of a pattern database (not shown) for application to the model, providing a user with a series of standard treatments as well as appropriate starting points for the user to design a custom treatment for the modeled eye.

The model, including the therapeutic parameters, can be solved at the reconciliation engine 74 to provide a predicted geometry of the eye given the therapeutic intervention. Once the predicted geometry has been determined, it can be displayed to the user at the user interface 76. Further, one or more parameters associated with the shape of the cornea in the determined geometry can be provided to an optical characterization component 78. The optical characterization component 78 calculates one or more properties of the eye, for example, as one or more optical power values and as a series of Zernike polynomials. For example, the apical power, $F_a$, is given by:

$$F_a = \frac{n_c - 1}{R_a} \qquad \text{Eq. 1}$$

where $R_a$ is the apical radius of curvature.

To analyze the tangential power, the anterior surface can be approximated as a conic equation about the z-axis (the elevation axis) and radius, r,—such as:

$$r = \sqrt{2R_a + z^2 - (ez)^2} \qquad \text{Eq. 2}$$

where e is the eccentricity and $R_a$ is the apical radius of curvature.

The local radius of curvature can therefore be computed as:

$$R = \sqrt{R_a^2 + (ez)^2} \qquad \text{Eq. 3}$$

The tangential power, F, can be determined from this value as:

$$F = \frac{n_c - 1}{R} \qquad \text{Eq. 4}$$

where $n_c$ is the refractive index of the cornea.

From these values, a prediction of the refractive error and optical aberrations for a given patient's eye after a given therapeutic intervention can be determined, allowing the intervention to be customized for the patient.

Figure 6:
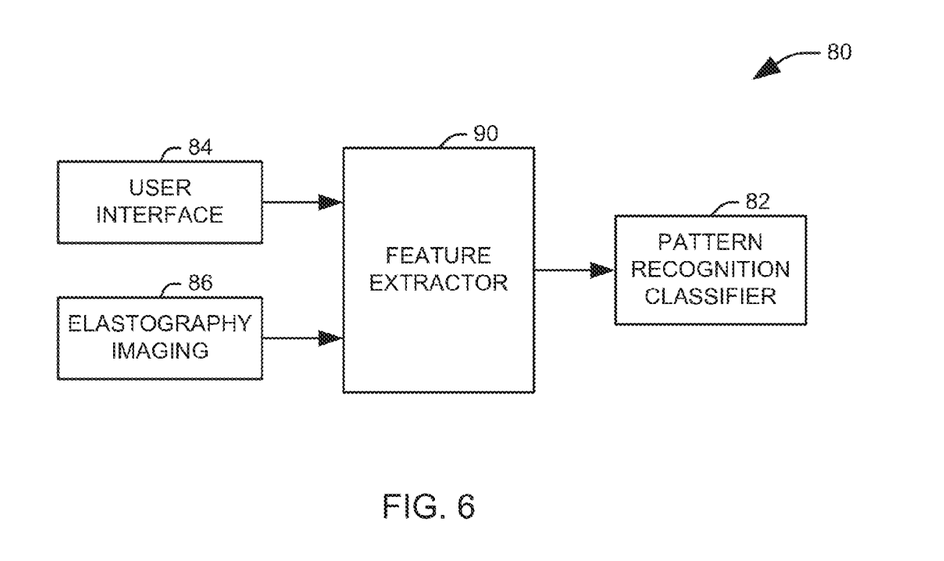
FIG. 6 illustrates a patient screening system for determining if a patient is an appropriate candidate for a therapeutic procedure in accordance with one aspect of the present invention

FIG. 6 illustrates a patient screening system 80 for determining if a patient is an appropriate candidate for a therapeutic procedure in accordance with one aspect of the present invention. For example, the patient screening system 80 can be designed to predict patient outcomes as a plurality of outcome classes for one or more therapeutic interventions, including refractive surgery, collagen cross-linking, or intracorneal ring insertion. It will be appreciated that various elements of the illustrated patient screening system 80 can be implemented as computer programs, executable on one or more general purpose computers. Accordingly, any structures herein described can be implemented alternately as dedicated hardware circuitry for the described function or as a program code stored as part of a computer-assessable memory, such as a computer hard drive, random access memory, or a removable disk medium (e.g., magnetic storage media, flash media, CD and DVD media, etc.). Functions carried out by the illustrated system, but not helpful in understanding the claimed invention, are omitted from this diagram. For example, a system implemented as a computer program would require some amount of working memory and routines for accessing this memory. Such matters are understood by those skilled in the art, and they are omitted in the interest of brevity.

It will further be appreciated that components of the patient screening system can be configured to interact with other software program modules. For example, a pattern recognition classifier 82 can run within a computer operating system environment, utilizing data libraries available from the operating system. Similarly, a given computer implemented element can receive data from one or more other program modules, and provide data to other program modules that utilize the system output. Furthermore, portions of the patient screening system 80 can reside on a remote computer system, whereby various system components and external resources can be linked via a computer network such as WAN, LAN, optical communication media, public switched telephone network, the global packet data communication network now commonly referred to as the Internet, any wireless network or any data transfer equipment offered by a service provider.

The patient screening system 80 comprises a user interface 84 that can also allow the user to introduce one or more parameters of interest, such as the age, sex, medical history, and other medically relevant information concerning the patient. Further, in accordance with an aspect of the present invention, the patient screening system 80 can comprise an elastography imaging device 86 configured to provide strain and stress data relating to the eye of the patient. For example, the elastography imaging device 86 can include an apparatus for applying a known perturbation (e.g., force, pressure, energy, or displacement) to the eye tissue, for example, through applanation or localized variance of air pressure. An accompanying force sensor can be provided to measure the force applied by the elastography imaging device. The eye tissue can be imaged, with any appropriate imaging modality (e.g., MRI or OCT), before and after the force is applied, or at a plurality of different forces, to provide a plurality of images of the eye. From these images, appropriate stress and strain data for the eye can be determined. Further, the elastography imaging device 86 can be utilized to determine a geometric profile of the eye. For the purpose of determining a geometry of the eye, the imaging device 86 can utilize magnetic resonance imaging (MRI), optical coherence tomography (OCT), Scheinpflug imaging, or any other appropriate imaging modality. The determined images can be supplemented by additional values, such as a measured corneal topography and a determined axial length of the eye. To this end, the elastography imaging device 32 can include, for example, an ultrasound imaging device or a partial coherence interferometer arrangement, for determining the axial length, as well as an appropriate imager for determining the corneal topography. It will be appreciated that, while the patient screening system 80, focuses on the effects of surgical and therapeutic intervention on the corneal and the resulting visual effects, the representation of the patient's eye can further include each of the sclera, the lens, the zonules, the choroid, the retina, the iris and, the ciliary body of the eye.

Each of the user interface 84 and the elastography imaging device 86 can provide appropriate data to a feature extractor 90 that extracts feature data from the provided data. The feature extractor 90 extracts feature values from each image according to a set of selected features. The selected features can be any values derived from the pattern that vary sufficiently among the various output classes to serve as a basis for discriminating among them. Numerical data extracted from the features can be conceived for computational purposes as a feature vector, with each element of the vector representing a value derived from one feature within the pattern. Specific features can be selected by any reasonable method, but typically, appropriate features will be selected by experimentation and prior success. For example, the feature extractor 90 can be configured to extract one or more parameters from data provided by the elastography imaging system 86. In the illustrated implementation, the image data provided by the elastography imaging component 86 can be digitized and processed to obtain an overall geometry of the eye. For example, the images can be filtered and one or more edge detection algorithms can be utilized to determine the boundaries of the various tissue layers. From the determined geometry, the feature extractor 90 can provide measurements, such as the thicknesses of various tissue layers within the eye, as well as calculated values, such as Zernike polynomials for the cornea and optical power values (e.g., apical and tangential values). Further, in accordance with an aspect of the present invention, and as described above in FIG. 2, the stress and strain values provided by the elastography imaging component 86 can be utilized to calculate one or more nonlinear measures of elasticity for the cornea at one or more locations. The measures can include hysteresis, creep, stress relaxation, and a strain dependent function for Young's modulus for any of a plurality of locations of interest within the eye, particularly the cornea and sclera.

Each of the determined values can be included as part of the extracted feature vector, as well as any of a number of values derived from this information. For example, in one implementation, a known displacement can be applied to the cornea in a first direction, and the displacement of the cornea in second and third directions, each perpendicular to the first direction and to one another, can be measured at a plurality of locations. For each location, a ratio of the measured displacement along the second direction to the known displacement along the first direction and a ratio of the measured displacement along the third direction to the known displacement along the first direction can be determined and provided as biomechanical parameters for the location Further examples of corneal features extracted from the imaging, elastography and modeling can be a spatial variation of corneal elasticity, measured, for example, as a parametric or nonparametric measure of variation (e.g., standard deviation) among a plurality of measured locations or as a gradient mapping of the cornea in one or more dimensions. Similarly, where the patient has already undergone a surgical or nonsurgical intervention, a difference in elasticity between sections subjected to collagen cross-linking or abnormal strains near the flap region after refractive procedure can be determined. Differences in biomechanical properties, including nonlinear viscoelasticity measures, from normal corneal tissue can also be determined for regions of residual stroma bed after a refractive surgery procedure. In addition, native heterogeneity within cornea is of interest during screening of patients, which can be measured, for example, as a measure of variation of one or more elasticity parameters or as a set of gradients determined from the measured values. For example, a maximum gradient or an average of a set of highest gradients can be utilized as a feature.

Additional features can include features representing various regions of the cornea and sclera. For example, features representing elasticity measures and gradients from various regions of the cornea, for example, the anterior portion or posterior portion of the cornea, as well as derived values (e.g., ratios and differences) intended to compare the properties of the two regions. Similar measures can be determined for a central portion of the cornea and a peripheral portion, and any other locations of interest for a given therapeutic procedure. Such regional features are of particular interest in detecting the onset of keratoconus, a known risk factor for refractive surgery, as regional and local abnormalities around stress/strain peaks can be detected. Accordingly, any of these derived parameters from the nonlinear elasticity data can be utilized as part of the feature vector, depending on the therapeutic intervention of interest for the patient screening system 80.

The extracted feature vector is then provided to the pattern recognition classifier 82. At the classifier, the feature vector, representing the patient's data, is, via an appropriate optimization algorithm, compared to training data representing each of a plurality of outcome classes. Any of a variety of optimization techniques can be utilized at the pattern recognition classifier for making this determination, including support vector machines, self-organized maps, fuzzy logic systems, data fusion processes, expert systems, rule, case based systems, or algorithmic programs, or any of a variety of neural network classifiers. Each outcome class represents a predicted range of outcomes for the patient given the application of the therapeutic procedure. This can range from a binary "good" and "bad" to a plurality of graduations of expected improvement. Ideally, the training data represents feature vectors and associated outcomes for previous patients, although data from a whole-eye model could be utilized initially in training and testing the classifier model. From the provided feature vector, an outcome class is selected and a confidence in the selected result can be calculated. Results falling below a threshold confidence value can be rejected.

Figure 7:
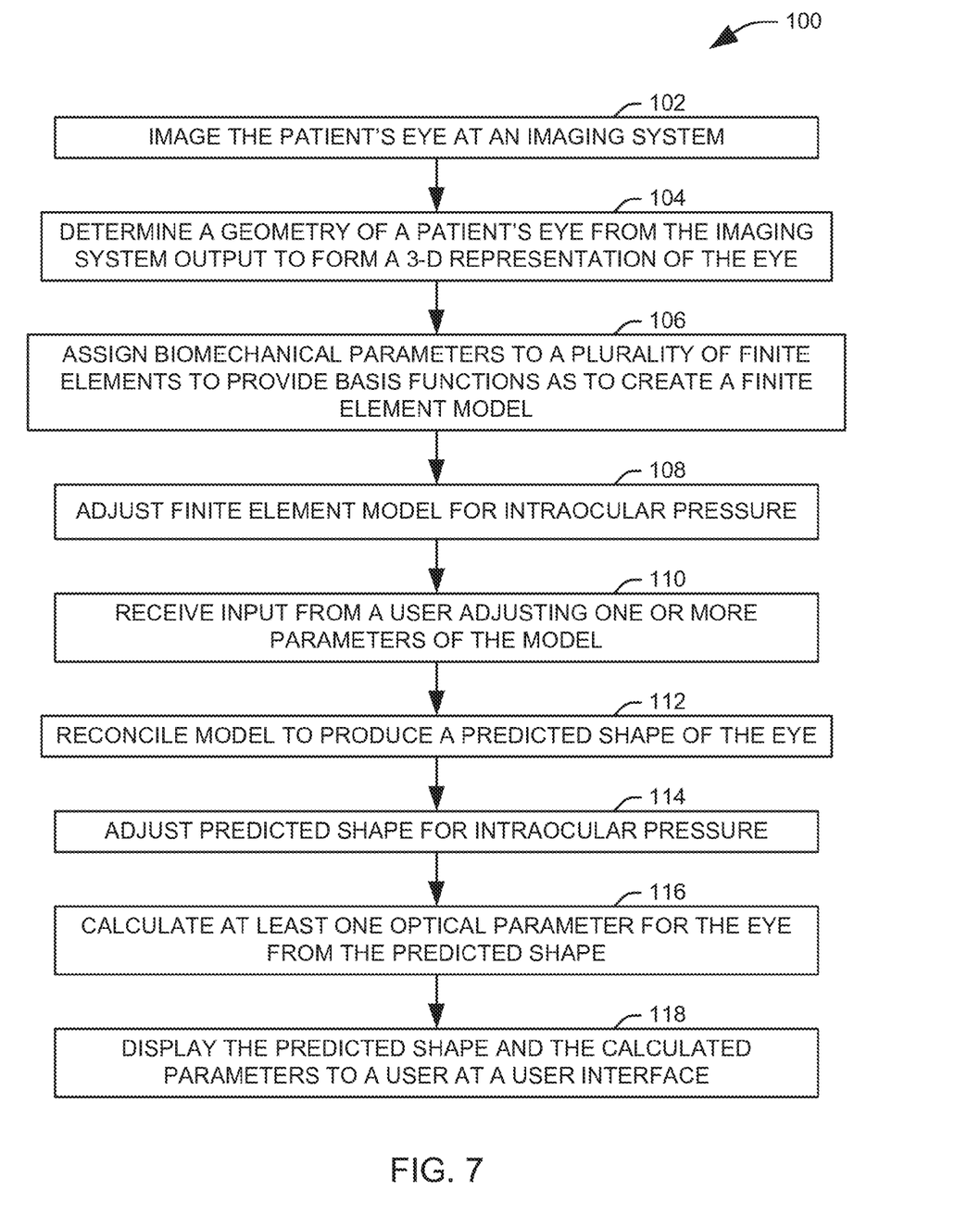
FIG. 7 illustrates a methodology for predicting the outcome of a surgical outcome in accordance with an aspect of the present invention.

In view of the foregoing structural and functional features described above, a methodology in accordance with various aspects of the present invention will be better appreciated with reference to FIG. 7. While, for purposes of simplicity of explanation, the methodology of FIG. 7 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect of the present invention.

FIG. 7 illustrates a methodology 100 for predicting the outcome of a surgical outcome in accordance with an aspect of the present invention. The methodology begins at step 102, where an eye of a patient is imaged by an imaging system. For example, the imaging system can include a magnetic resonance imaging system (MRI), a computer tomography (CT) system, or any other appropriate image system for determining a geometry of the eye. The image generated by the imaging system can be two-dimensional or three-dimensional. At step 104, the generated image is used to construct a representation of the geometry of the patient's eye. For example, a two-dimensional image can be axially rotated to provide a representation of the patient's eye. Standard thickness values for various tissue layers can used to simulate a three-dimensional model. Where a three-dimensional imaging of the whole eye has been performed, the geometry of the patient's eye can be derived directly from the imaging data.

At step 106, the three-dimensional representation is divided into a plurality of finite elements, each represented by an associated function. Biomechanical parameters of the eye tissue are assigned to the associated functions of the plurality of finite elements to provide a finite element model of the eye. The associated functions reflect the behavior of a given portion of the tissue under stress and strain from other portions of the eye and intraocular pressure. The biomechanical parameters representing the eye tissue can be determined via direct measurement or known representative results for each tissue can be utilized.

At step 108, the finite element model is adjusted to account for intraocular pressure. In accordance with an aspect of the present invention, distortions to the geometry of the eye caused by intraocular pressure can be determined, and a displacement of the corneal tissue can be added to the model to simulate an eye that is not distorted by intraocular pressure. In one implementation, the actual intraocular pressure and an elasticity of the cornea can be measured, and an appropriate adjustment can be applied, for example, from a table of known corneal deflections for given values of intraocular pressure.

At step 110, a user provides an alteration to the model that simulates the effects of a therapeutic procedure. For example, an appropriate pattern of changes to the geometry and biomechanical properties of the model can be selected at a graphical user interface to simulate one of a variety of refractive surgical procedures, an application of a collagen cross-linking treatment, or any other appropriate therapeutic intervention. In one implementation, the patterns can be customizable, allowing a user to customize a therapeutic procedure to produce optimal results.

At step 112, the finite element model is reconciled to incorporate the changes provided by the user to provide a predicted shape of the eye. At 114, the predicted shape is adjusted to reflect the presence of an appropriate amount of intraocular pressure. For example, a deflection to the cornea can be applied according to a measured corneal stiffness and intraocular pressure of the patient. From the predicted shape, at least one optical parameter can be calculated at step 116. For example, the predicted corneal shape can be characterized as a series of Zernike polynomials, and one or more optical power values can be calculated from the predicted shape. At step 118, the predicted shape and the calculated optical parameters are displayed to a user.

Figure 8:
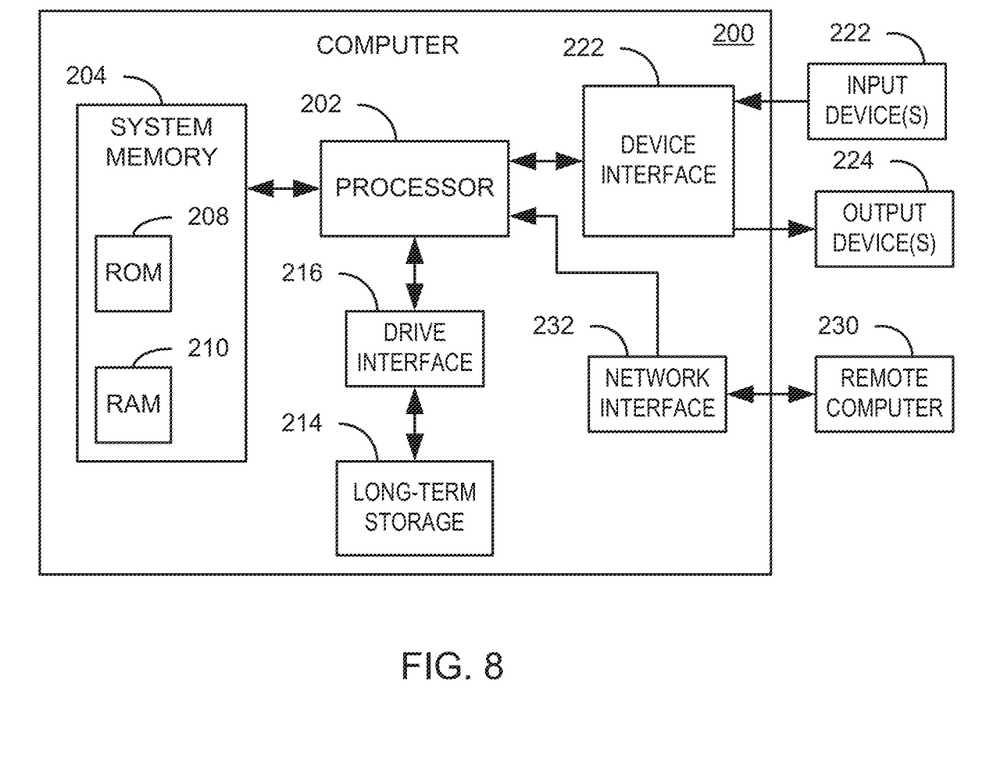
FIG. 8 illustrates a computer system that can be employed to implement systems and methods described herein, such as based on computer executable instructions running on the computer system.

FIG. 8 illustrates a computer system 200 that can be employed to implement systems and methods described herein, such as based on computer executable instructions running on the computer system. The computer system 200 can be implemented on one or more general purpose networked computer systems, embedded computer systems, routers, switches, server devices, client devices, various intermediate devices/nodes and/or stand alone computer systems. Additionally, the computer system 200 can be implemented as part of the computer-aided engineering (CAE) tool running computer executable instructions to perform a method as described herein.

The computer system 200 includes a processor 202 and a system memory 204. Dual microprocessors and other multi-processor architectures can also be utilized as the processor 202. The processor 202 and system memory 204 can be coupled by any of several types of bus structures, including a memory bus or memory controller, a peripheral bus, and a local bus using any of a variety of bus architectures. The system memory 204 includes read only memory (ROM) 208 and random access memory (RAM) 210. A basic input/output system (BIOS) can reside in the ROM 208, generally containing the basic routines that help to transfer information between elements within the computer system 200, such as a reset or power-up.

The computer system 200 can include one or more types of long-term data storage 214, including a hard disk drive, a magnetic disk drive, (e.g., to read from or write to a removable disk), and an optical disk drive, (e.g., for reading a CD-ROM or DVD disk or to read from or write to other optical media). The long-term data storage can be connected to the processor 202 by a drive interface 216. The long-term storage components 214 provide nonvolatile storage of data, data structures, and computer-executable instructions for the computer system 200. A number of program modules may also be stored in one or more of the drives as well as in the RAM 210, including an operating system, one or more application programs, other program modules, and program data.

A user may enter commands and information into the computer system 200 through one or more input devices 220, such as a keyboard or a pointing device (e.g., a mouse). These and other input devices are often connected to the processor 202 through a device interface 222. For example, the input devices can be connected to the system bus by one or several parallel ports, a serial port or a universal serial bus (USB). One or more output device(s) 224, such as a visual display device or printer, can also be connected to the processor 202 via the device interface 222.

The computer system 200 may operate in a networked environment using logical connections (e.g., a local area network (LAN) or wide area network (WAN) to one or more remote computers 230. A given remote computer 230 may be a workstation, a computer system, a router, a peer device or other common network node, and typically includes many or all of the elements described relative to the computer system 200. The computer system 200 can communicate with the remote computers 230 via a network interface 232, such as a wired or wireless network interface card or modem. In a networked environment, application programs and program data depicted relative to the computer system 200, or portions thereof, may be stored in memory associated with the remote computers 230.

It will be understood that the above description of the present invention is susceptible to various modifications, changes and adaptations, and the same are intended to be comprehended within the meaning and range of equivalents of the appended claims. The presently disclosed embodiments are considered in all respects to be illustrative, and not restrictive. The scope of the invention is indicated by the appended claims, rather than the foregoing description, and all changes that come within the meaning and range of equivalence thereof are intended to be embraced therein.

Having described the invention, the following is claimed:

1. A non-transitory computer readable medium, storing executable instructions for facilitating the design of a therapeutic intervention for an eye of a patient, the executable instructions comprising:
   a geometry generation element configured to form a three dimensional representation of the eye of the patient from received image data;
   a user interface configured to receive a plurality of therapeutic parameters defining a proposed therapeutic intervention for the eye of the patient from an associated input device;
   a reconciliation engine configured to:
      i. establish a finite element model of the eye of the patient, according to the determined geometry of the eye and at least one biomechanical parameter of the model for each of corneal tissue, sclera tissue, and at least one other structure of the eye;
      ii. alter at least one of a biomechanical parameter and the determined geometry of the eye according to the therapeutic parameters; and
      iii. solve the established model to determine a predicted geometry of the eye after the therapeutic intervention; and
   an optical characterization component configured to calculate at least one optical parameter from the predicted geometry.

2. The non-transitory computer readable medium of claim 1, the reconciliation engine being configured to establish a finite element model of the eye of the patient having no a priori restraints on the motion of a corneal limbus of the eye.

3. The non-transitory computer readable medium of claim 1, the reconciliation engine further being configured to correct the established finite element model for the effects of intraocular pressure, such that the established finite element model represents the eye of the patient in the absence of intraocular pressure.

4. The non-transitory computer readable medium of claim 1, the at least one biomechanical parameter comprising a nonlinear measure of the elasticity of each of the corneal tissue, the sclera tissue, and the at least one other structure of the eye.

5. The non-transitory computer readable medium of claim 1, the at least one optical parameter comprising one of an apical power of the eye and a tangential power of the eye.

6. The non-transitory computer readable medium of claim 1, the at least one optical parameter comprising a series of Zernike polynomials representing the shape of a cornea of the eye.

7. A patient screening system for determining if a patient is an appropriate candidate for a therapeutic procedure, comprising:\
   a parameter measurement element configured to generate stress and strain data for an eye of the patient;
   a processor; and
   a non-transitory computer readable medium storing executable instructions, the instructions comprising:
   a feature extractor configured to determine at least one nonlinear elasticity value representing the eye of the patient; and
   a pattern recognition classifier that classifies the patient into one of a plurality of classes, each representing a degree of risk expected for the patient, according to the at least one nonlinear elasticity value and at least one other parameter specific to the patient.

8. A system for predicting the results of a therapeutic intervention for an eye of a patient, comprising:
   an imaging system configured to provide image data representing at least a portion of the eye of the patient;
   an input device configured to permit a user to design a proposed therapeutic intervention for the eye of the patient, the therapeutic intervention comprising a proposed alteration of the image data as to simulate a change to the determined geometry of the eye;
   a parameter measurement system configured to detect a deflection of a plurality of regions of tissue of the eye of the patient under an applied stress to determine at least the gradient of a non-linear measure of viscoelasticity at each of the plurality of regions;
   a finite element modeling component configured to generate a finite element model representing a predicted geometry of the eye of the patient after the proposed therapeutic intervention according to the image data, the proposed therapeutic intervention, and the determined gradient of the non-linear measure of viscoelasticity at each of the plurality of regions; and
   a display configured to display the generated model to the user.

9. The system of claim 8, the finite element modeling component being configured to generate a finite element model according to the determined gradient of the non-linear measure of viscoelasticity in regions of each of corneal tissue, sclera tissue, and at least one other structure of the eye.

10. The system of claim 8, the parameter measurement system comprising an elastography imaging device configured to apply one of an acoustic perturbation and a pneumatic perturbation to the eye tissue.

11. The system of claim 8, the non-linear measure of viscoelasticity including a measured viscoelastic hysteresis of the eye tissue.

12. The system of claim 8, the non-linear measure of viscoelasticity including a stress relaxation property for the eye tissue.

13. The system of claim 8, the finite element modeling component comprising an optical characterization component configured to calculate at least one optical parameter from the predicted geometry.

14. The non-transitory computer readable medium of claim 1, the at least one other structure of the eye comprising the corneal limbus.

15. A system for predicting the results of a therapeutic intervention for an eye of a patient, comprising:

an imaging system configured to provide image data representing at least a portion of the eye of the patient;

an input device configured to permit a user to design a proposed therapeutic intervention for the eye of the patient, the therapeutic intervention comprising a proposed alteration of the at least one biomechanical property as to simulate a change in the material properties of at least a portion of the tissue comprising the eye;

a parameter measurement system configured to detect a deflection of a plurality of regions of tissue of the eye of the patient under an applied stress to determine at least the gradient of a non-linear measure of viscoelasticity at each of the plurality of regions;

a finite element modeling component configured to generate a finite element model representing a predicted geometry of the eye of the patient after the proposed therapeutic intervention according to the image data, the proposed therapeutic intervention, and the determined gradient of the non-linear measure of viscoelasticity at each of the plurality of regions; and a display configured to display the generated model to the user.

* * * * *